United States Patent
Daly (10) Patent No.: US 10,773,036 B2
(45) Date of Patent: Sep. 15, 2020

(54) RESPIRATORY TUBING SET

(71) Applicant: The Periodic Breathing Foundation, Providence, RI (US)

(72) Inventor: Robert W. Daly, Providence, RI (US)

(73) Assignee: The Periodic-Breathing Foundation, LLC, Indianapolis, IN (US)

( * ) Notice: Subject to any disclaimer, the term of this patent is extended or adjusted under 35 U.S.C. 154(b) by 523 days.

(21) Appl. No.: 14/073,422

(22) Filed: Nov. 6, 2013

(65) Prior Publication Data
US 2015/0122260 A1 May 7, 2015

(51) Int. Cl.
| | |
|---|---|
| *A61M 16/00* | (2006.01) |
| *A61B 5/097* | (2006.01) |
| *A61M 16/08* | (2006.01) |
| *A61B 5/083* | (2006.01) |
| *A61B 5/00* | (2006.01) |
| *A61M 16/12* | (2006.01) |
| *A61M 16/20* | (2006.01) |

(52) U.S. Cl.
CPC ....... *A61M 16/0045* (2013.01); *A61B 5/0836* (2013.01); *A61B 5/097* (2013.01); *A61B 5/4836* (2013.01); *A61M 16/0875* (2013.01); *A61M 16/12* (2013.01); *A61B 5/4806* (2013.01); *A61M 16/085* (2014.02); *A61M 16/205* (2014.02); *A61M 2202/0225* (2013.01); *A61M 2205/70* (2013.01)

(58) Field of Classification Search
CPC .............. A61M 16/0045; A61M 16/12; A61M 16/205; A61M 16/085; A61M 2202/0225; A61B 5/097; A61B 5/0836; A61B 5/4836

USPC .......... 128/204.23, 203.25, 205.28; 600/353
See application file for complete search history.

(56) References Cited

U.S. PATENT DOCUMENTS

| | | | |
|---|---|---|---|
| 7,900,626 B2* | 3/2011 | Daly ................. | A61M 16/0045 128/204.18 |
| 2007/0240718 A1* | 10/2007 | Daly ................. | A61M 16/0003 128/204.22 |
| 2008/0302364 A1* | 12/2008 | Garde ............... | A61M 16/0045 128/204.23 |
| 2009/0299430 A1* | 12/2009 | Davies ................. | A61B 5/0836 607/22 |
| 2012/0065533 A1* | 3/2012 | Carrillo, Jr. ............ | A61B 5/083 600/532 |
| 2013/0102916 A1* | 4/2013 | Colbaugh ............. | A61M 16/20 600/533 |
| 2014/0158124 A1* | 6/2014 | L'her ................... | A61B 5/0205 128/203.14 |

* cited by examiner

*Primary Examiner* — Samchuan C Yao
*Assistant Examiner* — Margaret M Luarca
(74) *Attorney, Agent, or Firm* — Barlow, Josephs & Holmes, Ltd.

(57) ABSTRACT

The present invention relates to a respiratory tubing set for controlling breathing of a patient. A tubing set for controlling breathing of a patient includes a respiratory conduit. The respiratory conduit is configured to be coupled to a patient interface device and is further configured to be coupled to a pressurized air generating device. The respiratory conduit includes at least two airflow control devices, positioned between the patient interface device and the pressurized air generating device that cooperate to closely control the $CO_2$ levels in the patient's bloodstream through the control of the patient's respiration.

8 Claims, 6 Drawing Sheets

RESPIRATORY TUBING SET

BACKGROUND OF THE INVENTION

The present invention relates generally to a system for the treatment of breathing disorders. In particular, the present invention relates to a tubing system for controlling breathing of a patient by maintaining specific levels of carbon dioxide ("$CO_2$") dissolved in the patient's arterial blood.

Sleep-disordered breathing ("SDB") includes all syndromes that pose breathing difficulties during sleep. These include obstructive sleep apnea ("OSA"), mixed sleep apnea ("MSA"), central sleep apnea ("CSA"), Cheyne-Stokes respiration ("CSR"), and others. Some form of SDB occurs in approximately 3-5% of the U.S. population.

While anatomical problems such as obesity or an abnormally narrow upper airway may be a cause of some SDB, neurological difficulties in controlling levels of blood gases, such as $CO_2$ and oxygen ("$O_2$"), are increasingly being recognized as important contributors to the SDB disease process. This is especially true of the "central" syndromes, such as MSA, CSA and CSR, which may collectively account for as much as 20% of all SDB. Changes in the neurological system that controls the blood gases often produce unsteady respiratory patterns that in turn cause arousals from sleep. These arousals are accompanied by severe spikes in blood pressure and release of stress hormones that may result in long-term damage to a number of organ systems. Additionally, some SDB syndromes involve abnormal overall levels of blood gases. For example, low levels of dissolved $CO_2$ in arterial blood are frequently encountered, which represents a clinical problem. Thus, there is a need to stabilize respiration and establish appropriate blood gas levels by restoring normal control of blood gases when treating SDB.

BRIEF SUMMARY OF THE INVENTION

In this regard, the present invention provides for a tubing system for controlling the breathing of a patient by maintaining specified levels of $CO_2$ in arterial blood. The system can be used to rectify inappropriate levels of both $CO_2$ and $O_2$ in arterial blood.

The system is generally directed to a respiratory tubing set. The respiratory tubing set is configured to be coupled at one end to a patient interface device that is coupled to a breathing airway, e.g., nose, mouth or both, of the patient. The respiratory conduit includes a primary airflow channel that includes a tap for monitoring variables in exhaled patient gasses and a secondary airflow channel that is terminated in a flow control device that is adjusted in response to the monitored variables in the monitoring tap. Initial rates of flow of an exhaled gas through the monitoring tap and the secondary airflow channel are calculated based on an expected rate of production of the gas by the patient, expected respiration rate of the patient, expected depth of respiration by the patient, and an expected concentration of the gas in the air expired by the patient.

As the flow rate of concentrated gas at the monitoring tap changes, the flow control device is adjusted to maintain a set flow rate at the monitoring tap. Preferably, the monitoring tap checks gas concentrations over a moving average in a manner that dampens the response and adjustment needs for the flow control device.

In one configuration, the respiratory tubing system includes a respiratory conduit configured to be coupled to a patient interface device at one end. The respiratory conduit is also configured to be coupled to a pressurized air supply device at an opposing end, wherein the pressurized air supply device supplies air to the patient. The respiratory tubing includes a primary airflow channel that includes a tap positioned in a gain chamber for monitoring variables in exhaled patient gasses and a secondary airflow channel that is terminated in a flow control. The amount of gas allowed to escape from the tubing set is determined by sizes of the valves and two volume connectors, pressure at which the pressurized air supply device operates, respiratory parameters of the patient (e.g., depth and frequency of breathing), production of gas by the patient per unit of time, and concentration of the gas in the patient's arterial blood.

In another example, a tubing set is provided as a system for controlling the exchange of $CO_2$ for a patient during breathing. The system includes a respiratory conduit. The respiratory conduit is configured to be coupled at one end to a patient interface device that is coupled to a breathing airway, e.g., nose, mouth or both, of the patient. The respiratory conduit is configured at the opposing end to remain open to the atmosphere or to be coupled to a pressurized air generating device. The respiratory conduit includes at least two air flow control devices, a first positioned at a predetermined point between the patient interface device at the first end of the respiratory conduit and the second end of the respiratory conduit and a second airflow control device positioned proximate the first end of the respiratory conduit and the patient interface. Rates of flow of a gas through the first air flow control device and the second air flow control device are initially set based on an expected rate of production of the gas by the patient, expected respiration rate of the patient, expected depth of respiration by the patient, and an expected concentration of the gas in the air expired by the patient. As expected outputs of $CO_2$ vary based on changes in respiration or patient metabolism, such changes are detected at the first airflow control device such that adjustments are made to the second airflow control device to bring the expected outputs of $CO_2$ back into the desired range.

A method for controlling flow of $CO_2$ to a patient during breathing is carried out as follows. The patient interface device is coupled to a $CO_2$ mixing device, which is coupled to air supply device; and the $CO_2$ mixing device includes multiple ventilation orifices interchangeably connected with multiple dead spaces, wherein the multiple ventilation orifices control supply of $CO_2$ to the patient and volume of $CO_2$ in the multiple dead spaces. The method includes measuring airflow through each of the multiple ventilation orifices; detecting a content of $CO_2$ in the measured airflow; adjusting airflow through each of the multiple ventilation orifices based on the detecting of the concentration of $CO_2$; and adjusting sizes of the multiple dead spaces based on the detection of the concentration of $CO_2$ and the adjusting of the airflow through each of the multiple ventilation orifices.

Further features and advantages of the invention, as well as structure and operation of various embodiments of the invention, are disclosed in detail below will reference to the accompanying drawings.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

Now referring to the drawings, the respiratory tubing set for controlling breathing is shown and generally illustrated in the figures. It is notable that of the two blood gases, carbon dioxide ("$CO_2$") and oxygen ("$O_2$"), problems with neurological control of breathing during sleep are primarily related to the control of $CO_2$ rather than $O_2$. $CO_2$ is dissolved in blood, and together with bicarbonate ions determines blood pH. Excessive $CO_2$ causes the blood to become acidic, while a deficit in $CO_2$ will cause the blood to be alkaline. Since proteins need a stable pH environment in which to function, the $CO_2$ levels should be controlled within a narrow range that will yield a blood pH of about 7.4. This is accomplished in the present invention through the close matching of $CO_2$ excretion via the lungs to the endogenous $CO_2$ production that is the product of cellular metabolism.

Figure 1:
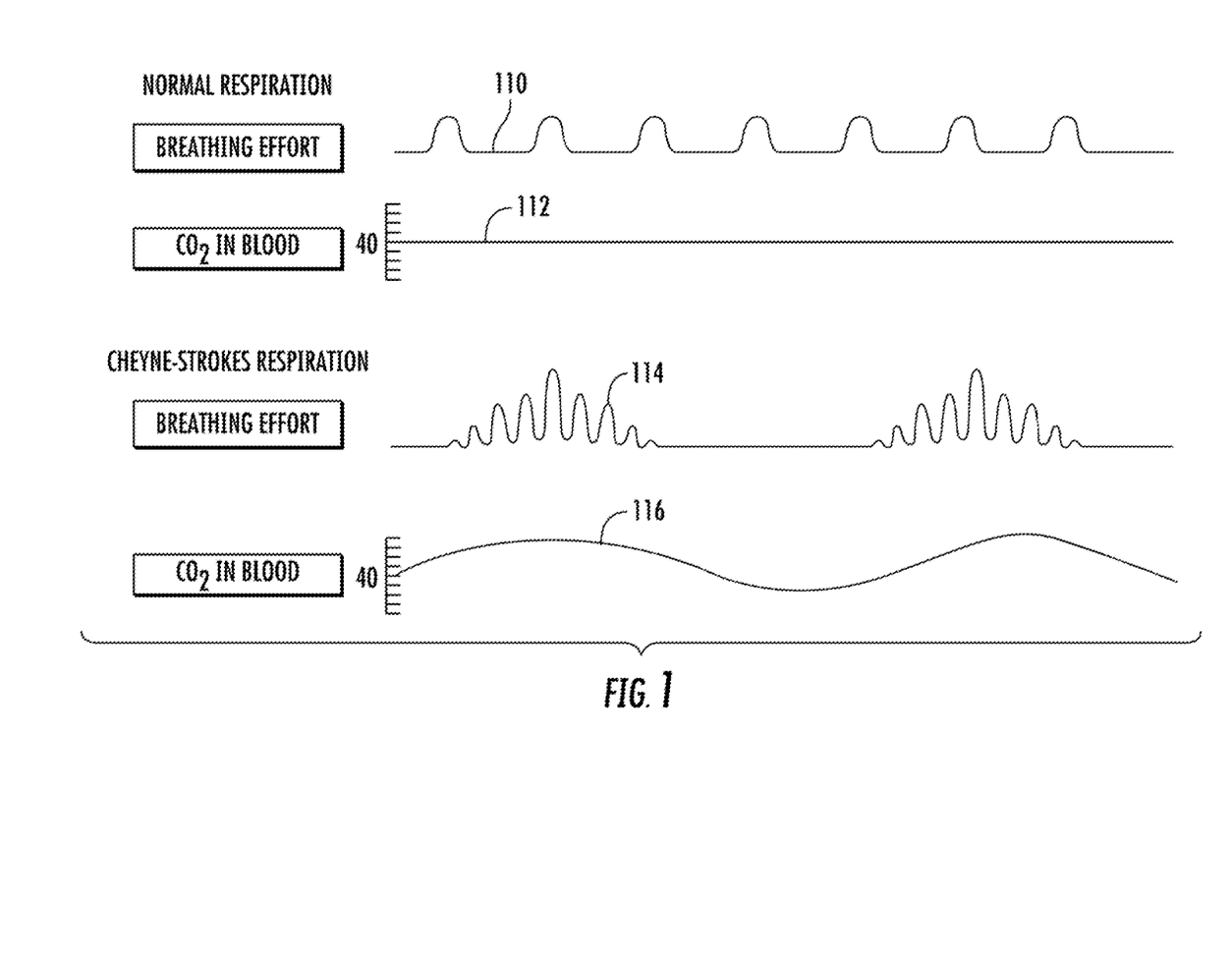
FIG. 1 is a graphical representation of a comparison between normal respiration and Cheyne-Stokes respiration.

FIG. 1 illustrates normal respiration and Cheyne-Stokes respiration plots along with corresponding $CO_2$ blood levels plots. During normal respiration, the breathing effort of a patient is steady, as shown by the plot 110. This corresponds to steady arterial $CO_2$ blood levels, shown in plot 112. A typical normal partial pressure of dissolved $CO_2$ in arterial blood is 40 mm Hg and $O_2$ pressure is approximately 105 mm Hg. During Cheyne-Stokes respiration, the patient's breathing effort is erratic, as illustrated by the waxing/waning plot 114. A corresponding plot 116 shows the associated variable blood $CO_2$ levels during Cheyne-Stokes respiration.

Within humans, a sensitive and finely tuned system detects blood $CO_2$ levels via a number of sensors, or chemoreceptors, located within the vasculature and the brain of the patient. Nerve signaling from these sensors is processed by respiratory control centers in the brain, which in turn send appropriate breathing pattern commands to the respiratory muscles including those of the diaphragm, chest and breathing airway. The goal of the system is to match the excretion of $CO_2$ with the production of $CO_2$ by varying the rate of respiration (both the depth and frequency of breathing). In healthy individuals, this system is accurate and steady. It is able to respond quickly to changes in $CO_2$ production and maintain blood $CO_2$ levels within a narrow range. Like many homeostatic mechanisms in the body, control of blood gases is accomplished by a closed-loop negative feedback control system.

When the system for controlling blood $CO_2$ becomes disordered, such as in CSR, it can lose its ability to maintain steady $CO_2$ levels. It "chases" blood $CO_2$ in an oscillating pattern of "overshoot" and "undershoot", resulting in a characteristic waxing/waning respiratory pattern. CSR is the classic syndrome associated with this disordered respiratory patterning and it is common in the setting of a heart failure. FIG. 1 illustrates that normal breathing is accompanied by stable $CO_2$ levels in arterial blood while CSR exhibits oscillating breathing patterns due to unstable $CO_2$ levels.

Since the waxing/waning respiratory drive associated with poor control of blood gases applies also to control of the muscles holding the airway open, cyclic airway collapse during the waning epoch of respiratory drive is often a feature of these syndromes. In fact, pure waxing/waning respiratory patterns not associated with at least intermittent airway collapse are relatively rare and MSA may be the dominant expression of respiratory instability. MSA may present as an extremely regular and predictable pattern of obstructive events associated with reduced respiratory effort but it may also present as a chaotic mixture of events of different kinds (e.g. obstructive apneas, central apneas, hypopneas) with no visually discernible pattern.

For several decades it has been possible to describe the necessary conditions for respiratory stability in mathematical terms. The analytical framework is identical to that used in classical process control theory for predicting the stability of a closed-loop negative feedback control system. While these systems are able stably to control very complex and sensitive processes if correctly tuned, certain categories of problems are known to cause instability and oscillating control that render the process useless or worse. In general, these problems are caused by an excessive sensitivity or "closed-loop gain" in the control loop and timing problems, where an excessive time delay is encountered in measuring the results of the process and taking the appropriate corrective action. These are the same problems that sufferers from unstable sleeping respiration often exhibit. Further, since the relationship between $CO_2$ excretion and tidal volume of the breath taken is substantially linear as depicted in the relationship at FIG. 2, the traditional CPAP arrangement is too efficient in clearing the $CO_2$ produced after exhalation causing further instability in the feedback loop.

It is well-established that the underlying cause of instability in the chemical control of respiration is usually excessive gain or sensitivity of one of the blood gas sensors, namely the peripheral chemoreceptor. The peripheral chemoreceptor is located within the carotid artery and directly samples arterial blood for oxygen and $CO_2$ content. The chemoreceptor is sensing the concentration of H+ ions in the blood, which is a proxy for $CO_2$ content in the arterial blood over a short period of time. The sensing becomes disordered and sends signals to the respiratory centers in the brain that tends to overestimate changes in blood gases, specifically, $CO_2$. Even though the cause of the disordered sensing is unknown, it is common in various diseases, e.g., heart failure. It is difficult to correct the above disordered sensing using current medical technology. Further, problems with blood circulation prolong the time delay in reporting changes in blood gases, which adds to the problem of instability in the patient's respiratory control loop.

Given that increased closed-loop gain in the respiratory control feedback loop resulting in unstable respiration is usually due either to excessively sensitive $CO_2$ sensors or impaired blood circulation, a number of therapeutic strategies have been attempted. Most existing therapies have various drawbacks.

Current therapeutic methods for restoring sleeping respiratory instability have the following problems:
 1. They are complicated.
 2. They are costly.
 3. They are inefficient in that they may reduce one aspect of the closed-loop respiratory control gain while increasing its other aspects. Further, they may fail to reliably reinstate conditions for stability.

4. They fail to enable a clinician to specify a target blood $CO_2$ range to be maintained during therapy where patients are currently hypocapnic.
5. They reduce an amount of oxygen available for breathing, necessitating an addition of supplemental oxygen in order to restore normal level of blood oxygen.
6. They fail to rapidly excrete CO2 under extraordinary circumstances, such as, after a prolonged obstructive apnea event.
7. They fail to respond immediately on a breath-by-breath basis to unstable respiratory patterns and rely on multi-breath pattern-recognition algorithms.
8. They rely on a single fixed estimate of respiratory requirements during the course of treatment and are not configured to adapt to variation in respiratory requirements.
9. They rely on expensive electronic equipment.

Figure 2:
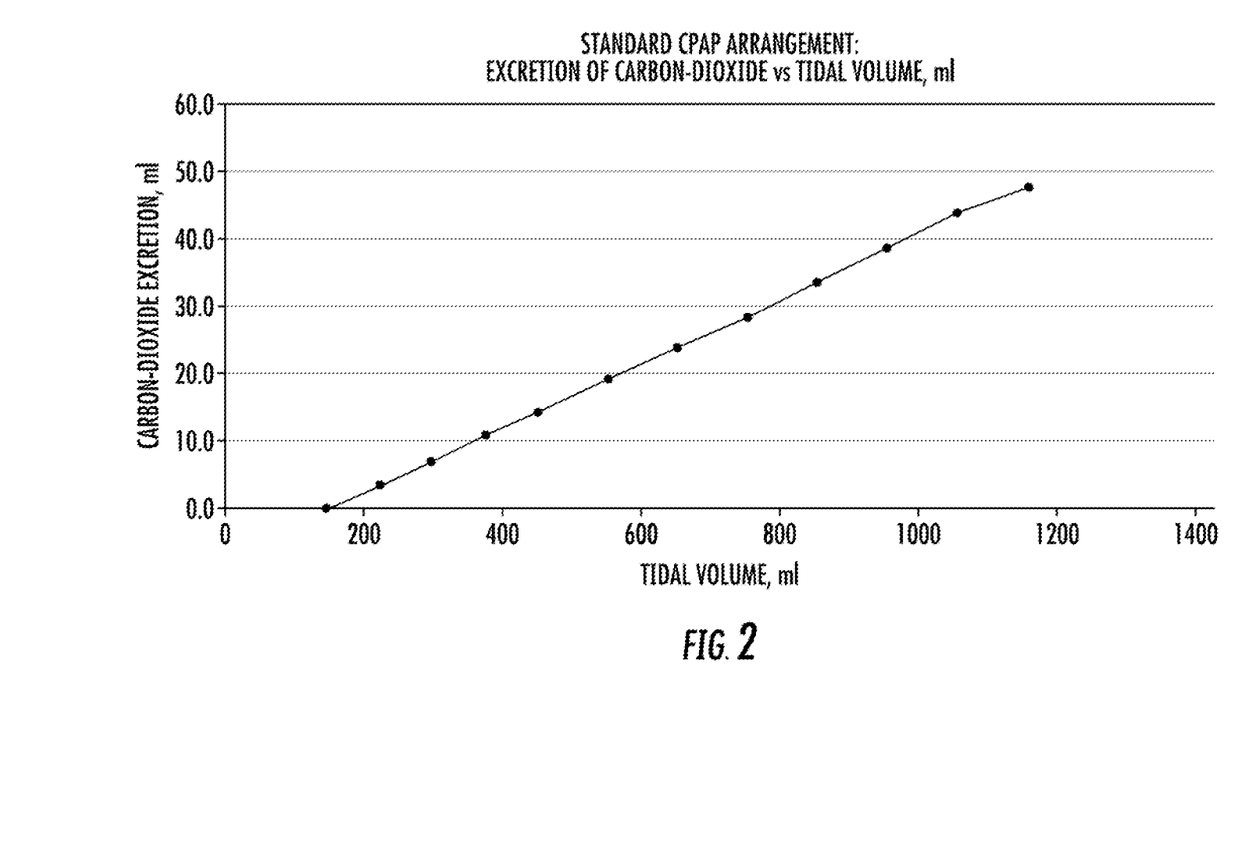
FIG. 2 is a graphical representation of typical $CO_2$ excretion by a patient using a CPAP system.

Current methods are also unable to permit modeling of the relationship between the rate of ventilation of the patient and the rate of $CO_2$ excretion in a non-linear fashion, instead as shown at FIG. 2 such relationships are typically linear. As a result the systems cannot accommodate the imposition of multiple distinct steps that permit "clamping" of respiration by maintaining $CO_2$ excretion within a defined range under most conditions.

The system and method capable of controlling breathing of a patient by maintaining certain levels of $CO_2$ in the patient's blood, while maintaining or improving blood oxygenation, described herein provide a solution to these problems. The present invention also provides a way to substantially eliminate "dead space gain". This issue is present in some conventional breathing systems.

Unstable breathing patterns consist of alternating hyperventilation and hypoventilation or apnea. During hyperventilation, there is rapid "blow-off" of $CO_2$ that causes a steep drop in arterial $CO_2$ that initiates an epoch of hypoventilation or even apnea when the arterial blood reaches the peripheral chemoreceptor and the brain detects an abnormally low level of blood $CO_2$. During the hypoventilation, $CO_2$ accumulates rapidly and again initiates an epoch of hyperventilation. This pattern can be repeated indefinitely.

Ideally, the lungs should be made to be less efficient during hyperventilation in order to resist the $CO_2$ blow-off. One of the ways to do this is to make the patient inhale a high percentage of $CO_2$ in inspired air, which will interfere with gas exchange in the lungs and therefore exhibit excessive excretion of $CO_2$. Likewise, the lungs should be maximally efficient during hypoventilation in order to limit the accumulation of $CO_2$. Thus, inhaled $CO_2$ is optimally zero during hypoventilation. Any design can be characterized in terms of its ability to exert a stabilizing influence by feeding the patient high concentrations of inspired $CO_2$ during hyperventilation and none during hypoventilation.

The features and advantages of the invention, as well as the structure and operation of various embodiments of the invention, are described in detail below with reference to the accompanying drawings. The invention is not limited to the specific embodiments described herein. Such embodiments are presented herein for illustrative purposes only. Additional embodiments will be apparent to persons skilled in the relevant art(s) based on the teachings contained herein.

While the present invention is described herein with reference to illustrative embodiments for particular applications, the invention is not limited thereto. Those skilled in the art with access to the teachings provided herein will recognize additional modifications, applications, and embodiments within the scope thereof and additional fields in which the present invention would be of significant utility.

Regulation of Blood Gas Levels

In accordance with the teachings herein, a respiratory tubing set 300 for controlling breathing of a patient are described. The respiratory tubing set 300 uses a controlled air passage wherein a process variable relating to blood gas concentration is measured and tracked to adjust a valve on a second air flow passage to control $CO_2$ levels in a patient's blood and, thereby, control breathing of the patient. The respiratory tubing set controls a relationship between the rate of ventilation (i.e., total minute volume, $V_E$) and the rate of $CO_2$ excretion ($V_{CO2}$) while permitting extensive modeling of this relationship in a non-linear, discontinuous fashion. This system allows a clinician to define a level of arterial blood $CO_2$ to be maintained during therapy as well as to place strong limits on both hyperventilation and hypoventilation. Under certain circumstances, the present invention can increase blood oxygenation without the use of supplemental oxygen.

The system provides an interaction between a controlled exhalation volume that results in discrete control over the volume of $CO_2$ and an inhalation dead space that results in rebreathing go $CO_2$ by the patient under treatment. Such interaction offers a possibility of defining a wide spectrum of relationships between the rate of ventilation and the rate of $CO_2$ excretion by the patient when used alone or in conjunction with a ventilatory assist device such as a Continuous Positive Airway Pressure ("CPAP") machine, which is set to a predetermined pressure. In an alternate embodiment, a ventilatory assist device is not used and the same effect is achieved using a simple device into which the patient breathes.

Figure 3:
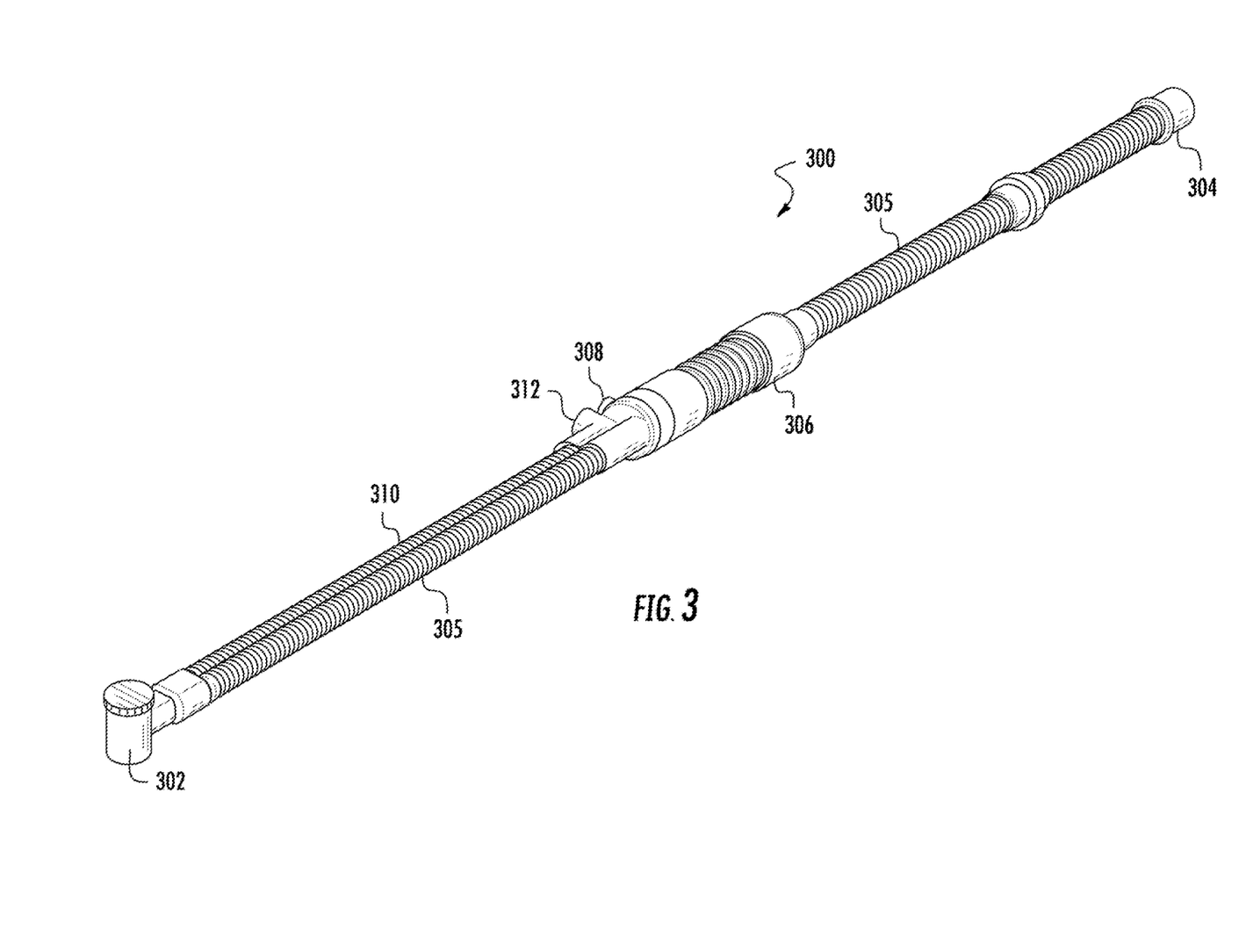
FIG. 3 is an illustration of the respiratory tubing set of the present invention.
Figure 4:
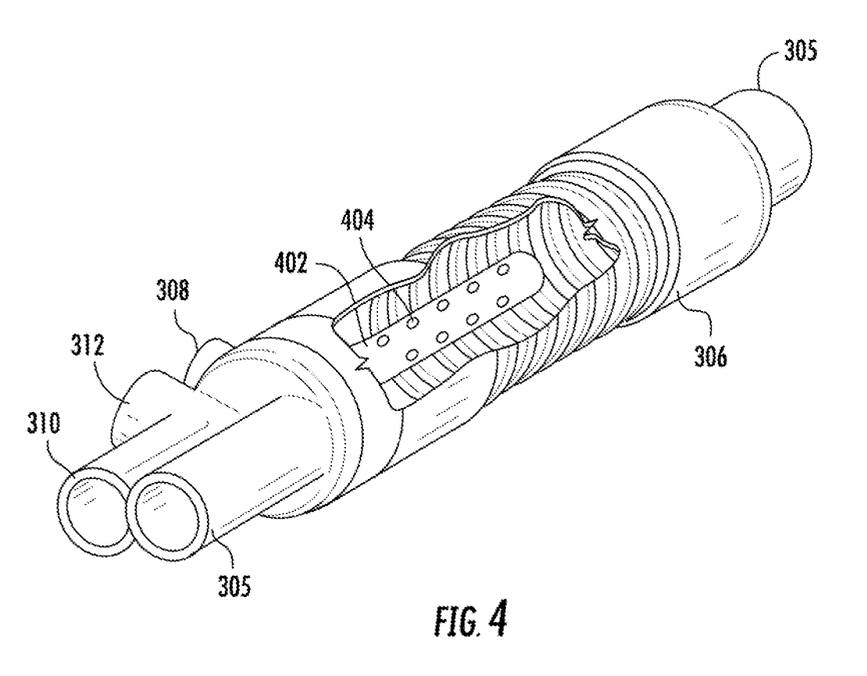
FIG. 4 is a cut away view of the gain chamber and monitoring port in the respiratory tubing set of the present invention.

As seen in FIG. 3 a respiratory conduit, is configured to attach to a patient interface device (e.g., a sealed CPAP mask) as a first end 302. The opposing end 304 may ventilate to free air or preferably interfaces with a CPAP machine (or any other air supply device). A primary flow channel 305 extends from the first end 302 at the patient interface device to the opposing end 304. A gain chamber 306 is provided in the primary flow channel 306 which contains a monitoring tap 308. As can be seen in the cutaway vice of the gain chamber 306 at FIG. 4, the monitoring tap 308 extends into a tube 402 the gain chamber 306 and ventilation orifices 404 are provide to allow the outflow of $CO_2$ that is exhaled by the patient.

Figure 5:
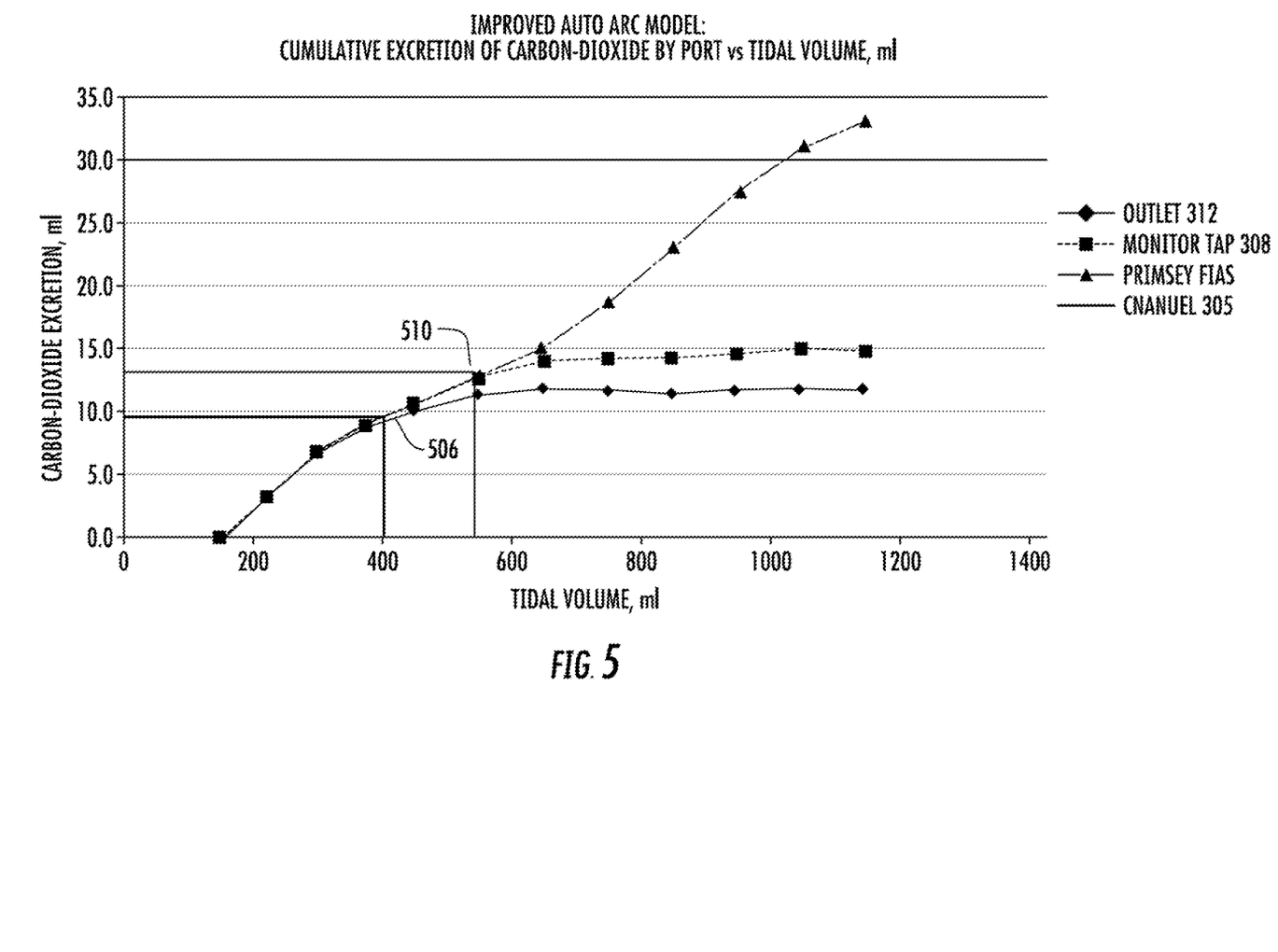
FIG. 5 is a graphical representation of controlled plateau of $CO_2$ excretion by the patient using the respiratory tubing set of the present invention.

Returning to FIG. 3 a secondary flow channel 310 also extends from the first end 302 at the patient interface to an outlet at 312. In operation, when coupled with a CPAP device positive pressure is generated on the primary flow channel 305. As the patient breathes inhalation gas is drawn inwardly at the patient interface at 302. When exhaling, exhalation gasses flow along both the primary flow channel 305 and the secondary flow channel 310 and is controlled in a manner as will be discussed in detail below. The lengths and/or volumes of the primary flow channel 305, the secondary flow channel 310 and the gain chamber 306 represent a distinct dead space or quasi-dead space volume. As air containing $CO_2$ is expelled from the patient's lungs into the respiratory conduit, a pressure generated by the CPAP machine causes at least some of the air and $CO_2$ contained in such air to flow out of the monitoring tap 308 and the outlet 312 in a specific pattern. The pattern depends on the volume of each one of patient's breaths or tidal volume ($V_T$) and the frequency of breathing, or respiration rate. Each breath consists of an expiratory interval and an inspiratory interval. Once the expiratory interval is over, inspiration commences and most or all of the remaining $CO_2$ in the conduit is re-breathed by the patient. Depending on the volume of each dead space and the size of each ventilatory orifice, the curve describing a relationship between the rate of ventilation and the rate of $CO_2$ excretion has an arbitrary number of inflection points defining line or curve segments (See, FIG. 5), each with a different slope and length.

The above system permits extensive modeling of the relationship between a patient's breathing (i.e., ventilation) and excretion of $CO_2$. Using conventional computer simulation techniques, the sizes of orifices, volumes, and/or configuration of the two are specified to establish a relationship that serves to return the respiratory control feedback loop to a stable operation. Since during the interval prior to falling asleep, $CO_2$ production may be high relative to the levels anticipated to prevail during sleep, an auxiliary ventilation valve is fitted that permits the patient to increase airflow through the device until comfortably resting in bed.

Figure 6:
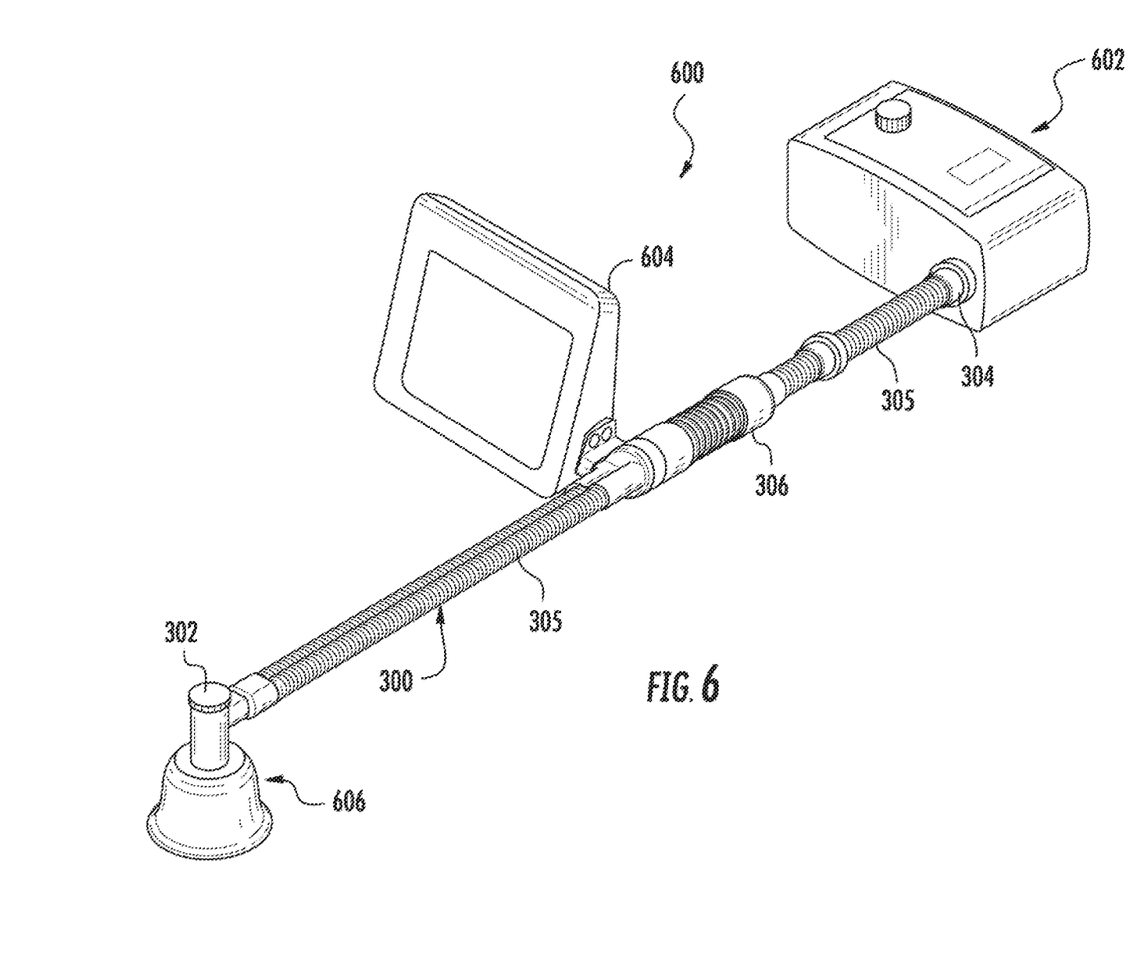
FIG. 6 is an illustration of a system incorporating the respiratory tubing set of the present invention.

FIG. 6 illustrates an exemplary system 600 for controlling breathing of a patient 101. The system 600 includes a respiratory tubing set 300 configured to be coupled to mask and headgear assembly at 302 and to a pressurized air supply device or CPAP device 602 at 304. The mask 606 and headgear assembly are known in the art. Such a mask 606 typically includes multiple straps that secure the mask to the face of patient so that there is a substantially sealed connection between the mask 606 and the patient's breathing airway (e.g., nose or mouth). The sealed interface or connection prevents uncontrolled leakage of air or gases from openings that may occur between the patient's face and the mask. As understood by one of ordinary skill in the art, other ways of securing the mask 606 to the patient are encompassed herein. A pressurized and/or nonpressurized gaseous substance (including air, gas, etc.) generating device, e.g., the CPAP device 602, can be used with the respiratory tubing set 300.

The mask is a sealed orofacial non-invasive ventilation mask. For example, the mask can be a Mirage NV Full Face Mask with adjustable VELCRO® strap headgear, as manufactured by ResMed Corp., Poway, Calif. A full-face mask can be used to cover both the nose and the mouth. This design eliminates mouth leak, permitting therapy for patients who breathe through the mouth and/or the nose. As can be understood by one of ordinary skill in the art, other types of masks can be used, such as a nasal mask, an oral mask, an orofacial mask, a nasal prong device, an intra-oral device, an endotracheal tube, or any other device.

The mask is affixed to the tubing set 300 at 302. This design allows a certain volume of air to escape from the mask per unit of time. The outflow at the monitoring tap 308 and outlet 312 has a variable size, which can be altered depending on the amount of air intended to be allowed to escape from the tubing set 305. In one example, monitoring tap 308 and the outlet 312 each permits air flow of 0.5-6 liters per minute, when the tubing set 300 is pressurized by the CPAP machine 602 at a specific pressure. This pressure can be equal to the patient's CPAP pressure prescription.

The tubing set 300 is connected to a controller 604 such that the monitoring tap 308 and the outlet 312 are routed into the controller 604 where they terminate in control valves 608 and 610. The monitoring tap 308 and the outlet 312 are each configured to allow escape of air at a specific rate via the control valves 608 and 610 when the pressurized air supply device 602 is operated at a specific pressure. Depending on the concentration of gas in the air flowing through each of the orifices, the gas will be escaping through each control valve 608 and 610 at a specific rate. The control valves 608 and 610 can be fixed, variable, or a combination of fixed and variable. As can be understood by one having ordinary skill in the art, varying locations and/or numbers of fixed and variable orifices can be used as desired. This allows a predetermined amount of air and gas (depending on the concentration of the gas in such air) to escape from the monitoring tap 308 and the outlet 312. Further, in case of variable control valves 608 and 610, their sizes can be manually or dynamically controlled. When manually controlled, a patient, a clinician, or someone else can control the flow and, thus, the amount of gas allowed to escape from the monitoring tap 308 and the outlet 312. When automatically controlled, the flow can be adjusted automatically by the controller 604 based on an amount of gas exhaled by the patient, amount of gas escaping from the monitoring tap 308 and the outlet 312, patient physical parameters (such as blood pressure, body mass, age, etc.) and/or other factors.

In initially establishing use of the respiratory tubing set 300, the flow volume permitted at the monitoring tap 308 and the outlet 312 can be preliminary determined using an algorithm based on patient's estimated high and low $V_{CO2}$ (rate of production of $CO_2$ in ml per minute) as directly measured during sleep. Alternatively, the patient's estimated high and low $V_{CO2}$ can be derived from patient's body mass or any other physiological or demographic variable or combination of variable. The sizes of volumes and monitoring tap 308 and the outlet 312 settings are adjusted during a polysomnographic study in a clinic, hospital, laboratory, or any other facility that is equipped with $CO_2$ monitoring equipment. Based on the adjustment, a final combination of monitoring tap 308 and the outlet 312 and volumes is determined. This combination establishes a first respiratory plateau (See, FIG. 5, segment 506) at or below a value of $V_{CO2}$ equal to the minimum estimated $CO_2$ production per minute expected to occur during sleep and a second respiratory plateau (See, FIG. 5, segment 510) at or above a value of $V_{CO2}$ equal to the maximum estimated $CO_2$ production per minute expected to occur during sleep.

As s known in the art an anti-asphyxiation valve and any number of auxiliary valves that can assist a patient during non-sleep breathing may be provided. An auxiliary valve, when opened, provides a substantial washout of the exhaled $CO_2$ from the tubing set. In one example, the patient can operate the auxiliary valve in order to provide $CO_2$ washout until patient is resting comfortably. The auxiliary valve can be closed manually by the patient or automatically after a certain period of time elapsed.

The anti-asphyxiation valve opens when the operating pressure of the CPAP machine 602 falls below a predefined value (i.e., CPAP machine 602 fails to provide adequate pressure). When the latter occurs, the anti-asphyxiation valve opens and allows the patient to breathe ambient air through the valve. Hence, the valve prevents asphyxiation of the patient in the event of failure of the CPAP machine 602.

Referring back to FIG. 6, the monitor tap 308 is coupled to the controller 604 that allows measurement of CO2 content in the air flowing from any one of or a combination of the monitoring tap 308 and the outlet 312. The data is used to adjust the rates of airflow the outlet 312. In combination, the monitoring tap 308 and the outlet 312 are configured to allow a specific, measured rate of escaping gases based on the rates of the supply air flow (either via pressure or vacuum) and the predicted metabolic rate of the patient. In an initial set-up for example, the flow of gasses out of the monitoring tap 308 and the outlet 312 may be set for example at an outflow of 4 l/min. The outflowing gasses are monitored at the $CO_2$ detector in controller 604 such that the $CO_2$ output is preferably maintained at 1% of the mixed gas output. More preferably, the process variable in terms of percentage CO2 output is monitored via the monitoring tap 308 at the gain chamber 603. Should the CO2 output vary beyond a predetermined range, the controller 604 adjusts the flow at outlet 312 either increase or decrease the outflow of gasses until the CO2 output returns to the set range.

In the case of CSR such an adjustment is made on a gradual basis as the metabolism of the patient changes instead of on a breath by breath monitoring. However, certain disordered breathing conditions result in random breathing rhythms such that the present invention can operate to clamp each breath of the patient as well.

As can be understood by one having ordinary skill in the art, varying locations and/or numbers of fixed and variable orifices can be used as desired. This allows a predetermined amount of air and gas (depending on the concentration of the gas in such air) to escape from the orifices in case of fixed orifices' sizes or a variable amount of gas to escape from the orifices in case of variable orifices' sizes. Further, in case of variable orifices, their sizes can be manually or dynamically controlled. When orifice sizes are manually controlled, a patient, a clinician, or someone else can control the size of the orifice and, thus, the amount of gas allowed to escape from the orifice. When orifice sizes are automatically controlled, their sizes can be adjusted automatically based on an amount of gas exhaled by the patient, amount of gas escaping from each specific orifice, patient physical parameters (such as blood pressure, body mass, age, etc.) and/or other factors.

In an exemplary setting, the present invention allows for 2-2.5% improvement in oxyhemoglobin saturation in a patient as compared to free breathing of ambient air. Since the oxyhemoglobin saturation curve is flat at its high end, this represents an important increase in available oxygen at the perfused tissues. Further, the present invention potentially obviates a need for supplemental oxygen in a number of medical settings. Also, by increasing oxygenation the present invention may reduce the sensitivity of the peripheral chemoreceptor, which causes most periodic breathing syndromes.

The present invention forces an increase in the depth of breathing and, thus, the overall rate of ventilation, since the first orifice is configured to saturate at a level that is insufficient to permit excretion of all $CO_2$ being produced by the patient. The patient breathes deeply enough to push $CO_2$ through the first dead space volume, so that $CO_2$ exits the device through at least the second orifice or at the gain chamber. By the time patient's inspiratory interval commences, the exhaled gas in various dead space volumes has been replaced with air and, thus, the concentration of oxygen in the inspired air is only slightly lower than that in the ambient air. Taking the two things together, the increase in breathing more than offsets the slight decline in oxygen content of inspired air ($F_{IO2}$) to produce greater oxygen transport in the lungs. Conventional single proximal dead space produces a decrease in $F_{IO2}$ that more closely matches or exceeds the increase in ventilation and therefore, a frequent need for supplemental oxygen. This is because the dead space is filled with exhaled breath and remains filled until inhalation commences. Conventional single distal dead space neither increases ventilation nor decreases $F_{IO2}$ versus normal breathing, thus, there should be no change in oxygen saturation.

The present invention, can be used in the following areas:

1. Recovery from carbon monoxide poisoning. The systems and methods of the present invention speed up the rate of clearance of CO by three to five times relative to the conventionally available methods (e.g., giving oxygen).

2. Prevention of hypocapnia during birth. Hyperventilation by the delivering mother is very common and cuts oxygen supply to the fetus substantially due to a sharp drop in CO2. Low CO2, or hypocapnia, inhibits oxygen transport in many ways. The present invention improves oxygen flow to the fetus during delivery.

3. Recovery from altitude sickness/mountain climbing. The present invention systems and methods without use of the CPAP machine allows quick recovery from this condition.

4. Recovery from ventilator dependency. It is often difficult to wean patients from ventilator dependency, which is a cause of death in a critical care setting. The present invention stimulates breathing and increases oxygenation of the patient allowing the patient to quickly recover.

5. Recovery from anesthesia. This is similar to the recovery from ventilator dependency.

6. Obviating the use of supplemental oxygen in certain chronic lung diseases. Chronic obstructive pulmonary disease is very common and requires expensive oxygen therapy. However, with the present invention there is no need to use such oxygen therapy.

7. As can be understood by one having ordinary skill in the art, other uses of the present invention's systems and methods are possible.

Example embodiments of the methods, circuits, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A tubing set for controlling breathing of a patient comprising:
   a first end received in communication with a patient's airway;
   a primary flow channel extending between the first end and an air supply;
   a gain chamber positioned in said primary flow channel;
   a monitoring tap extending from said gain chamber and terminating in a first variable flow control valve, said first variable flow control valve being calibrated to a patient's metabolic rate; and
   a secondary flow channel extending from the first end and terminating in a second variable flow control valve; and
   a controller to adjust said first and second variable flow control valves,
   wherein a volume of exhaled gasses from said patient is controlled with said first and second variable flow control valves.

2. The tubing set of claim 1, wherein said controller includes a $CO_2$ detector said controller adjusting said second variable flow control valve in response to a reading at said $CO_2$ detector.

3. The tubing set of claim 1, wherein said controller includes a $CO_2$ detector said controller predicting a metabolic rate of said patient based on the $CO_2$ concentration in said exhaled gasses said controller adjusting at least one of said first and second variable flow control valves in response to said metabolic rate.

4. The tubing set of claim 1, further comprising:
a means for establishing an airflow through said tubing set.

5. The tubing set of claim 4, said means for establishing airflow through said tubing set comprising a pressurized air supply device.

6. The tubing set of claim 4, said means for establishing airflow through said tubing set comprising a vacuum pump.

7. The tubing set of claim 1, wherein said controller monitors a process variable via the monitoring tap and adjusts the second control valve to increase or decrease the flow therethrough until the process variable returns to a predetermined range.

8. The tubing set of claim 7, wherein said process variable is $CO_2$.

\* \* \* \* \*